US012655948B2

(12) United States Patent
Van Bommel

(10) Patent No.: US 12,655,948 B2
(45) Date of Patent: Jun. 16, 2026

(54) LED TUBULAR LIGHTING DEVICE

(71) Applicant: SIGNIFY HOLDING B.V., Eindhoven (NL)

(72) Inventor: Ties Van Bommel, Horst (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/875,387

(22) PCT Filed: Jun. 12, 2023

(86) PCT No.: PCT/EP2023/065681
§ 371 (c)(1),
(2) Date: Dec. 16, 2024

(87) PCT Pub. No.: WO2023/242132
PCT Pub. Date: Dec. 21, 2023

(65) Prior Publication Data
US 2025/0198574 A1     Jun. 19, 2025

(30) Foreign Application Priority Data
Jun. 16, 2022     (EP) ..................................... 22179352

(51) Int. Cl.
*F21K 9/27* (2016.01)
*A61L 2/10* (2026.01)
(Continued)

(52) U.S. Cl.
CPC ................ *F21K 9/27* (2016.08); *F21K 9/272* (2016.08); *F21K 9/278* (2016.08); *H05B 45/20* (2020.01);
(Continued)

(58) Field of Classification Search
CPC . F21K 9/27; F21K 9/272; F21K 9/278; F21Y 2113/30
See application file for complete search history.

(56) References Cited

U.S. PATENT DOCUMENTS

2010/0219428 A1* 9/2010 Jung ......................... F21K 9/64
257/E33.056
2021/0270427 A1* 9/2021 Kim ......................... F21K 9/27
(Continued)

FOREIGN PATENT DOCUMENTS

CN          204201519 U      3/2015
WO          2015066069 A1    5/2015
WO          2021217147 A1    10/2021

*Primary Examiner* — William N Harris

(57) ABSTRACT
A light-emitting diode, LED, tubular lighting device (1) is disclosed, comprising an elongated hollow tubular member (2) and a plurality of LEDs. The plurality of LEDs comprise at least a plurality of first LEDs (10), wherein each of the first LEDs (10) is configured to emit violet light, and a plurality of second LEDs (11, 12, 13), wherein each of the second LEDs (11, 12, 13) is configured to emit ultraviolet light. The LED tubular lighting device (1) comprises an elongated carrier (8) arranged within the elongated hollow tubular member (2). The plurality of LEDs are arranged in at least one succession on the elongated carrier (8), wherein the plurality of LEDs are arranged in the at least one succession such that the distance between consecutive LEDs in the at least one succession varies over the at least one succession while the distance between consecutive first LEDs (10) in the at least one succession is constant over the at least one succession.

14 Claims, 3 Drawing Sheets

(51) Int. Cl.

| | |
|---|---|
| *A61L 9/20* | (2006.01) |
| *F21K 9/272* | (2016.01) |
| *F21K 9/278* | (2016.01) |
| *F21Y 113/00* | (2016.01) |
| *F21Y 115/10* | (2016.01) |
| *H05B 45/20* | (2020.01) |

(52) U.S. Cl.
CPC . *A61L 2/10* (2013.01); *A61L 9/20* (2013.01); *A61L 2202/11* (2013.01); *A61L 2209/12* (2013.01); *F21Y 2113/30* (2023.05); *F21Y 2115/10* (2016.08)

(56) References Cited

U.S. PATENT DOCUMENTS

| | | | |
|---|---|---|---|
| 2021/0404646 A1* | 12/2021 | Wang | F21V 33/0064 |
| 2022/0001069 A1 | 1/2022 | Allen et al. | |
| 2022/0282840 A1* | 9/2022 | Van Bommel | F21S 4/20 |
| 2024/0360966 A1* | 10/2024 | Xie | F21V 3/02 |
| 2024/0366825 A1 | 11/2024 | Van Bommel et al. | |

\* cited by examiner

LED TUBULAR LIGHTING DEVICE

CROSS-REFERENCE TO PRIOR APPLICATIONS

This application is the U.S. National Phase application under 35 U.S.C. § 371 of International Application No. PCT/EP2023/065681, filed on Jun. 12, 2023, which claims the benefit of European Patent Application No. 22179352.4, filed on Jun. 16, 2022. These applications are hereby incorporated by reference herein.

TECHNICAL FIELD

The present invention relates to a light-emitting diode (LED) tubular lighting device including an elongated carrier and a plurality of LEDs arranged on the elongated carrier.

BACKGROUND

It is desired to protect people from the spread of pathogens, e.g., bacteria or viruses such as influenza, or against the outbreak of novel viruses such as the recent COVID-19. Disinfection has become a topic of renewed interest as the demand for sterilization increases. For example, in medical facilities, disinfection of medical instruments and other medical equipment is important to reduce the transmission of pathogens and prevent the spread of illnesses between individuals.

In WO 2015/066069 a linear lamp is provided having one or more light emitting elements provided therein. The light emitting elements are directed to emit light in a direction different from the primary direction of the illumination of the lamp. The light emitting elements may be supported by a supporting optical element. The supporting optical element may permit the transmission of light therethrough. The supporting optical element may be an integral window upon which the light emitting elements are disposed.

SUMMARY

Disinfection can be accomplished by means of using violet light. Another way of disinfecting involves the use of ultraviolet (UV) light. As a response to pathogenic outbreaks involving airborne microorganisms, it would be beneficial to employ violet or UV light for disinfecting air and objects at locations where transmission of such microorganisms is believed to occur.

In view of the above, a concern of the present invention is to provide a device capable of providing lighting for general illumination purposes, and which device is also capable of providing a disinfection effect during operation.

To address at least one of this concern and other concerns, a light-emitting diode (LED) tubular lighting device in accordance with the independent claim is provided. Preferred embodiments are defined by the dependent claims.

In the context of the present application, the term "light" may not be limited to visible light, but may encompass at least ultraviolet radiation, which accordingly may be referred to as "ultraviolet light" herein.

According to a first aspect of the present invention, a LED tubular lighting device is provided. The LED tubular lighting device may provide light, which may be referred to as device light. The LED tubular lighting device comprises an elongated (hollow) tubular member having a first end and a second end. The elongated hollow tubular member comprises a light exit surface which extends at least in part between the first end and the second end. The LED tubular lighting device comprises a plurality of LEDs. Each of the plurality of LEDs is configured to, in operation, emit light. The plurality of LEDs comprise at least a plurality of first LEDs, wherein each of the first LEDs is configured to emit violet light having a dominant peak wavelength in the range 380 nm-420 nm. The plurality of LEDs comprise a plurality of second LEDs, wherein each of the second LEDs is configured to emit ultraviolet light having a dominant peak wavelength in the range 100 nm-380 nm. The LED tubular lighting device comprises an elongated carrier. The elongated carrier is arranged within the elongated hollow tubular member. The plurality of LEDs are arranged in at least one succession on the elongated carrier such that at least some of the violet light emitted by the plurality of first LEDs and at least some of the ultraviolet light emitted by the plurality of second LEDs is emitted from the LED tubular lighting device via the light exit surface, e.g., as the device light. The plurality of LEDs are arranged in the at least one succession such that the distance between at least some consecutive LEDs in the at least one succession varies over the at least one succession while the distance between consecutive first LEDs in the at least one succession is constant, or substantially constant, over the at least one succession.

The distances between consecutive ones of the plurality of LEDs in the at least one succession and the distances between consecutive first LEDs in the at least one succession may be referred to as the pitch of the plurality of LEDs in the at least one succession and the pitch of the first LEDs in the at least one succession, respectively. Thus, the pitch of the plurality of LEDs in the at least one succession (e.g., over the length of the elongated carrier) may vary over the at least one succession, while the pitch of the plurality of first LEDs may be constant, or substantially constant, over the at least one succession.

By the plurality of LEDs being arranged in the at least one succession such that the distance between consecutive LEDs in the at least one succession varies over the at least one succession while the first LEDs are arranged in the at least one succession such that the distance between consecutive first LEDs in the at least one succession is constant over the at least one succession, a homogeneous or uniform distribution of violet light over or along the light exit surface may be achieved. At the same time, disinfection using UV light can be provided in a reliable and cost-effective manner. According to one or more embodiments of the present invention, LEDs configured to emit violet light can be used for providing violet light and bactericidal disinfection, possibly instead of LEDs configured to emit white light (which may not be included in the LED tubular lighting device), while LEDs configured to emit UV light can be used for providing virucidal disinfection.

In the context of the present application, by the plurality of LEDs being arranged in the at least one succession such that the distance between at least some consecutive LEDs in the at least one succession varies over the at least one succession, it may be meant that a distance between a pair of consecutive LEDs in the at least one succession differs from the distance between at least one other pair of consecutive LEDs in the at least one succession by at least 30%, for example by at least 50%, or even by at least 100%. Further in the context of the present application, by the distance between consecutive first LEDs in the at least one succession being constant, or substantially constant, over the at least one succession, it may be meant that the distances between consecutive first LEDs in the at least one succession vary by not more that 25%, for example by not more than 15%, or even by not more than 5%.

Further in the context of the present application, a distance between a first LED and a second LED (e.g., consecutive LEDs) in the at least one succession may be defined as a distance between center points of the respective ones of the first and second LEDs, or as a distance between a side or edge of the first LED facing the second LED and a side or edge of the second LED facing the first LED, for example.

By the inclusion of the elongated hollow tubular member, the LED tubular lighting device may have an elongated form.

The light exit surface may extend along the length of the elongated hollow tubular member.

The succession(s) of the plurality of LEDs may for example be directed along or in parallel with a longitudinal direction of the LED tubular lighting device, the elongated hollow tubular member and/or the elongated carrier.

A length of the LED tubular lighting device (e.g., in a longitudinal direction thereof) may for example be (about) 0.6 m, 0.9 m, 1.2 m or 1.5 m. It is noted that these lengths are exemplifying, and the LED tubular lighting device could have a length that is between two of the disclosed example lengths, or a length that is less than 0.6 m or exceeding 1.5 m.

The elongated hollow tubular member may for example be made at least in part, or entirely, of quartz.

The elongated carrier may for example be flexible. The elongated carrier may for example comprise at least one printed circuit board (PCB), such as, for example, at least one flexible PCB. In alternative or in addition, the elongated carrier may for example comprise at least one flexible foil.

The plurality of LEDs may for example comprise at least twenty first LEDs. The plurality of LEDs may for example comprise at least eight second LEDs.

Possibly, the plurality of LEDs may only include the plurality of first LEDs and the plurality of second LEDs. That is, the plurality of LEDs may consist of the plurality of first LEDs and the plurality of second LEDs. LEDs configured to emit light within a certain wavelength range may be excluded from the plurality of LEDs. For example, LEDs configured to emit white light may not be included in the plurality of LEDs. By the plurality of LEDs not including any LEDs configured to emit white light, the perceived visibility of the violet light emitted by the LED tubular lighting device for a user/viewer may be relatively high, as white light may decrease the perceived visibility of violet light for a user/viewer.

In the context of the present invention, the violet light may be light having a wavelength within a wavelength range from 380 nm to 420 nm, the ultraviolet light may be light having a wavelength within a wavelength range from 100 nm to 380 nm.

For example, the violet light may be light having a wavelength 405 nm±5 nm. Violet light with wavelength in this wavelength range may provide particularly good bactericidal effect compared to violet light with other wavelengths (or wavelength ranges). Light having a wavelength 405 nm±5 nm is relatively safer than light with wavelength<400 nm and more effective in disinfection compared to light with wavelength>410 nm.

The at least one succession may extend between the first end and the second end. The LED that is closest to the first end and the LED that is closest to the second end may not be second LEDs. Possibly, the LED that is closest to the first end and the LED that is closest to the second end may be first LEDs. At each or any of the first and second ends of the elongated hollow tubular member there may be an opening. Each or any of the openings may provide access to the interior of the elongated hollow tubular member. Each or any of the openings may be closed by means of an end closure, e.g., including a cap, that may be included in the LED tubular lighting device and which may be arranged at the corresponding one of the first and second ends. End closures such as caps may to some extent be degraded by exposure to ultraviolet light. By the LED that is closest to the first end and the LED that is closest to the second end not being second LEDs, but instead, e.g., first LEDs, any degradation of any end closures such as caps by exposure to ultraviolet light may be reduced or even avoided.

Each or any of the second LEDs may be configured to emit ultraviolet light having a dominant peak wavelength in the ultraviolet wavelength C range. By one or more of the plurality of second LEDs being configured to emit ultraviolet light having a dominant peak wavelength in the ultraviolet wavelength C range, a virucidal effect may be achieved by the light emitted by the LED tubular lighting device. Ultraviolet light having a dominant peak wavelength in the ultraviolet wavelength C range is effective in inactivating viruses.

Each or any of the second LEDs may be configured to emit ultraviolet light having a dominant peak wavelength in the ultraviolet A wavelength range and/or in the ultraviolet B wavelength range, but possibly not in the ultraviolet C wavelength range. Ultraviolet light having a dominant peak wavelength in the ultraviolet wavelength A range is effective in inactivating bacteria.

At least one of the second LEDs may be configured to emit ultraviolet light having a dominant peak wavelength in the ultraviolet A wavelength range. At least one of the second LEDs may be configured to emit ultraviolet light having a dominant peak wavelength in the ultraviolet B wavelength range. At least one of the second LEDs may be configured to emit ultraviolet light having a dominant peak wavelength in the ultraviolet C wavelength range.

At least one of the second LEDs configured to emit ultraviolet light having a dominant peak wavelength in the ultraviolet C wavelength range may be arranged in the at least one succession between at least one of the second LEDs configured to emit ultraviolet light having a dominant peak wavelength in the ultraviolet A wavelength range and at least one of the second LEDs configured to emit ultraviolet light having a dominant peak wavelength in the ultraviolet B wavelength range.

According to one or more example implementations, each of any second LED configured to emit ultraviolet light having a dominant peak wavelength in the ultraviolet C wavelength range may be arranged in the at least one succession between first LEDs, which first LEDs may be immediately neighboring the said second LED in the at least one succession.

There may be a larger number of second LEDs configured to emit ultraviolet light having a dominant peak wavelength in the ultraviolet B wavelength range included in the LED tubular lighting device compared to the number of second LEDs configured to emit ultraviolet light having a dominant peak wavelength in the ultraviolet C wavelength range included in the LED tubular lighting device.

There may be a larger number of second LEDs configured to emit ultraviolet light having a dominant peak wavelength in the ultraviolet A wavelength range included in the LED tubular lighting device compared to the number of second LEDs configured to emit ultraviolet light having a dominant peak wavelength in the ultraviolet B wavelength range included in the LED tubular lighting device.

Each or any of the plurality of second LEDs may be configured to emit ultraviolet light having a dominant peak wavelength in the far ultraviolet C wavelength range, e.g., between 200 nm and 230 nm.

In case one or more of the plurality of second LEDs are configured to emit ultraviolet light having a dominant peak wavelength in the ultraviolet C wavelength range, then these may be arranged in the at least one succession such that they are at or approximately at a position in the middle between the first and second ends, or at or approximately at a center position of the elongated carrier.

In the context of the present invention, the ultraviolet A (UVA) wavelength range may be from 315 nm to 380 nm, the ultraviolet B (UVB) wavelength range may be from 280 nm to 315 nm, and the ultraviolet C (UVC) wavelength range may be from 100 nm to 280 nm.

Further in the context of the present invention, the far ultraviolet C wavelength range may be from 200 nm to 230 nm.

The elongated hollow tubular member may for example be made of a material that is transmissive to light in the ultraviolet C wavelength range.

The light exit surface may have at least one diffuser. By such a configuration, the relatively unsafe ultraviolet light may become well distributed (e.g., in many directions with respect to the LED tubular lighting device). Further, the violet light in the light emitted by the LED tubular lighting device may be very visible to a user.

The at least one diffuser may for example comprise a diffusing coating. In alternative or in addition the at least one diffuser may comprise a surface having a selected degree of surface roughness so as to attain a certain capacity of the at least one diffusing portion to diffuse or scatter light imping-ing thereon. The at least one diffuser may for example have a reflectance in a range between 10% and 30%, or between 12% and 30%, or between 10% and 25%, preferably between 12% and 25%. A reflectance in a range between 12% and 25% may be preferable in terms of striking a balance between safety and disinfection performance versus reliability. A relatively high reflectance may be desired for achieving a relatively high disinfection performance and safety. On the other hand, a relatively high reflectance may result in substantial back reflection, which may entail that UV light is reflected back to the LEDs and/or the elongated carrier such as a PCB, which may degrade over time due to being exposed to UV light.

The plurality of first LEDs and the plurality of second LEDs may be arranged in the at least one succession such that the distance between consecutive second LEDs in the at least one succession is larger than the distance between consecutive first LEDs in the succession over at least a part of the at least one succession. In other words, the pitch of the plurality of second LEDs in the at least one succession may be larger than the pitch of the plurality of first LEDs in the at least one succession. By such a configuration, a relatively high reliability of the LED tubular lighting device (e.g., lifetime) may be achieved. A relatively high intensity of UV light may not be desired as it may cause negative impact on any electrical connections in the LED tubular lighting device and/or the plurality of LEDs.

The plurality of first LEDs may be arranged over the entirety of the at least one succession. The plurality of second LEDs may be arranged over only a part of the at least one succession. For example, the at least one succession may be extending between the first and second ends, and first LEDs may be arranged over the entirety of the at least one succession between the first and second ends, while only part of the at least one succession may include second LEDs. By such a configuration, a relatively high safety and reli-ability of the LED tubular lighting device (e.g., lifetime) may be achieved. The violet light in the light emitted by the LED tubular lighting device may be clearly visibly to a user while the intensity of the UV light in the light emitted by the LED tubular lighting device may be relatively low in particular parts of the LED tubular lighting device where components thereof may be susceptible to UV light.

Each of the first LEDs may be configured to emit violet light having a same intensity. At least some of the second LEDs may be configured to emit ultraviolet light having different intensity. By such a configuration, a relatively high safety and reliability of the LED tubular lighting device (e.g., lifetime) may be achieved. The violet light in the light emitted by the LED tubular lighting device may be clearly visibly to a user while the intensity of the UV light in the light emitted by the LED tubular lighting device may be relatively low in particular parts of the LED tubular lighting device where components thereof may be susceptible to UV light.

Each or any of the first LEDs may be configured to emit violet light having a constant intensity. Possibly, all of the first LEDs could be configured to emit violet light having a same intensity. The constant intensity may for example be specified by an installer of the LED tubular lighting device. That is, upon installation of the LED tubular lighting device, each or any of the first LEDs may be arranged, e.g., by the installer of the LED tubular lighting device, to emit violet light having a constant intensity.

At least some of the second LEDs may be configured to emit ultraviolet light having different intensity and/or dif-ferent wavelengths within the ultraviolet light wavelength range (e.g., from 100 nm to 380 nm), which for example may be specified by an installer of the LED tubular lighting device at the time of installation of the LED tubular lighting device. Possibly, for each or any of the second LEDs, the intensity and/or wavelength of the ultraviolet light emitted by the second LED may be changed dynamically during operation, e.g., based on desired intensity and/or wavelength of the ultraviolet light emitted by the LED tubular lighting device and based on measurements of these quantities by a sensor. The sensor may either be included in the LED tubular lighting device or be arranged externally with respect to the LED tubular lighting device (e.g., separate from the LED tubular lighting device).

Each or any of the plurality of LEDs may be configured to emit light having a wavelength less than or equal to 420 nm. For example, each of the plurality of LEDs may be configured to emit light having a wavelength less than or equal to 420 nm and equal to or greater than 100 nm.

The elongated carrier may comprise a major surface. The plurality of LEDs may be arranged on the major surface.

The elongated carrier may comprise a first major surface and a second major surface oppositely arranged from the first major surface. Some of the plurality of LEDs may be arranged on the first major surface and the other ones (e.g., the remaining ones) of the plurality of LEDs may be arranged on the second major surface. According to one or more example implementations, the plurality of LEDs may be arranged on a first major surface of the LED tubular lighting device, and another or other components of the LED tubular lighting device may be arranged on another major surface of the elongated carrier oppositely arranged from the first major surface. Such other component(s), which may be comprised in the elongated carrier, may for example include electrical components which may be part of one or more controllers which may be comprised in the LED tubular lighting device. By such a configuration, any component(s) of the LED tubular lighting device other than the plurality of LEDs may be protected from UV light to which they may be susceptible.

As mentioned above, the LED tubular lighting device may comprise a controller (or several controllers). The controller(s) may be configured to control operation of each of the plurality of LEDs at least with respect to switching on and/or switching off the LED. The controller may be configured to individually control each of the first plurality of LEDs. The controller may be configured to individually control each of the second plurality of LEDs. The controller may be configured to control operation of each of at least some of the plurality of LEDs with respect to intensity and/or wavelength of the light emitted by the LED. For example, the controller may be configured to control operation of each of some or all of the plurality of second LEDs with respect to intensity and/or wavelength of the light emitted by the second LED. Possibly, for each or any of the second LEDs, the controller may be configured to control the intensity and/or wavelength of the ultraviolet light emitted by the second LED, e.g., based on desired intensity and/or wavelength of the ultraviolet light emitted by the LED tubular lighting device and based on measurements of these quantities by a sensor. The sensor may either be included in the LED tubular lighting device or be arranged externally with respect to the LED tubular lighting device (e.g., separate from the LED tubular lighting device). According to one or more example implementations, the controller may be configured to individually control the intensity of violet light emitted by the plurality of first LEDs and the intensity of ultraviolet light emitted by the plurality of second LEDs, wherein a ratio between the intensity of violet light emitted by the plurality of first LEDs and the intensity of ultraviolet light emitted by the plurality of second LEDs may be varied by the controller.

The controller, which in alternative could be referred to as a control unit, a control device, etc., may for example include or be constituted by any suitable central processing unit (CPU), microcontroller, digital signal processor (DSP), Application Specific Integrated Circuit (ASIC), Field Programmable Gate Array (FPGA), etc., or any combination thereof. The controller may optionally be capable of executing software instructions stored in a computer program product e.g. in the form of a memory. The memory may for example be any combination of read and write memory (RAM) and read only memory (ROM). The memory may comprise persistent storage, which for example can be a magnetic memory, an optical memory, a solid state memory or a remotely mounted memory, or any combination thereof.

The controller may for example comprise driver circuitry for controlling supply of power to the plurality of LEDs and/or for controlling operation of the plurality of LEDs. The driver circuitry may for example comprise LED driver circuitry configured to drive (or control) one or more of the plurality of LEDs. The controller may be configured to control operation of each or any of the plurality of LEDs for example by way of transmitting at least one control signal or control message or the like to the LED(s).

A surface of the elongated carrier on which the plurality of LEDs are arranged may be covered by a reflective material or reflective element configured to reflect ultraviolet light impinging on the reflective material or reflective element. The reflective material or reflective element may have a reflectance of at least 85%, preferably at least 90%, in at least part of the ultraviolet C wavelength range. The reflective material or reflective element may for example include microporous Polytetrafluoroethylene (PTFE), which may have a reflectance of at least 90% in at least part of the ultraviolet C wavelength range.

The elongated carrier may be reflective. The elongated carrier may for example at least in part be covered with a reflective material, e.g., a material that is reflective for light in the ultraviolet C wavelength range. The material that is reflective for light in the ultraviolet C wavelength range may for example include PTFE or the like. The reflective material may for example be in the form of particles. The elongated carrier may for example at least in part be covered with PTFE particles.

In one or more embodiments, at least one of the second LEDs may be configured to emit ultraviolet light having a dominant peak wavelength in the near ultraviolet C wavelength range (i.e., 240 nm-280 nm). This type of UVC light is relatively more effective in terms disinfection compared to other UVC wavelength ranges.

In one or more embodiments, at least one of the second LEDs may be configured to emit ultraviolet light having a dominant peak wavelength in the short ultraviolet C wavelength range (i.e., <240 nm). This type of UVC light is relatively safer compared to other UVC wavelength ranges.

In one or more embodiments, at least one of the second LEDs may be configured to emit ultraviolet light having a dominant peak wavelength in the ultraviolet C wavelength range is arranged in the at least one succession between at least one of the first LEDs.

In one or more embodiments, at least one of the second LEDs may be configured to emit ultraviolet light having a dominant peak wavelength in the ultraviolet B wavelength range is arranged in the at least one succession between at least one of the first LEDs.

In one or more embodiments, at least one of the second LEDs may be configured to emit ultraviolet light having a dominant peak wavelength in the ultraviolet A wavelength range is arranged in the at least one succession between at least one of the first LEDs.

The first end and the second end of the elongated hollow tubular member may for example comprises pins, which may be configured to mechanically and electrically connect the LED tubular lighting device to a luminaire or lamp.

According to a second aspect, a luminaire or lamp, comprising at least one LED tubular lighting device according to the first aspect, is provided.

Each or any one of the LEDs may for example include or be constituted by an inorganic LED and/or an organic LED (OLED). Solid state light emitters are relatively cost-efficient light sources since they in general are relatively inexpensive and have a relatively high optical efficiency and a relatively long lifetime. Examples of LEDs include semiconductor, organic, or polymer/polymeric LEDs, optically pumped phosphor coated LEDs, optically pumped nanocrystal LEDs or any other similar devices as would be readily understood by a person skilled in the art. For example, the term LED can encompass a bare LED die arranged in a housing, which may be referred to as a LED package. According to another example, the term LED can encompass a Chip Scale Package (CSP) LED, which may comprise a LED die directly attached to a substrate such as a PCB, and not via a sub-mount. The term LED can for example encompass a laser diode, because a laser diode is a diode which emits light.

Further objects and advantages of the present invention are described in the following by means of exemplifying embodiments. It is noted that the present invention relates to all possible combinations of features recited in the claims. Further features of, and advantages with, the present invention will become apparent when studying the appended claims and the description herein. Those skilled in the art realize that different features of the present invention can be combined to create embodiments other than those described herein.

BRIEF DESCRIPTION OF THE DRAWINGS

Exemplifying embodiments of the invention will be described below with reference to the accompanying drawings.

Figure 1:
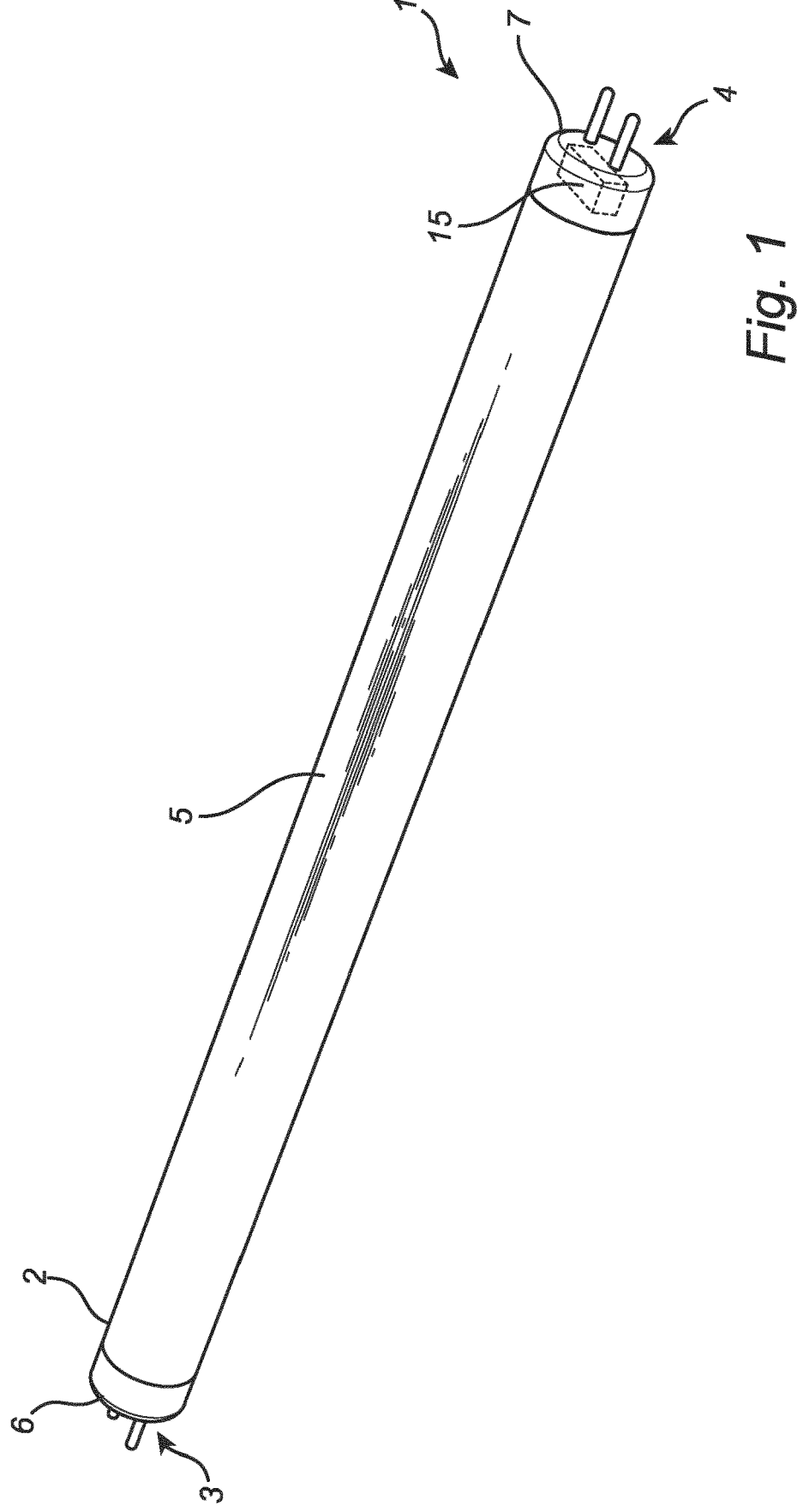
FIG. 1 is a schematic side view of a light-emitting diode (LED) tubular lighting device according to an embodiment of the present invention.

All the figures are schematic, not necessarily to scale, and generally only show parts which are necessary in order to elucidate embodiments of the present invention, wherein other parts may be omitted or merely suggested.

DESCRIPTION WITH REFERENCE TO THE DRAWINGS

The present invention will now be described hereinafter with reference to the accompanying drawings, in which exemplifying embodiments of the present invention are shown. The present invention may, however, be embodied in many different forms and should not be construed as limited to the embodiments of the present invention set forth herein; rather, these embodiments of the present invention are provided by way of example so that this disclosure will convey the scope of the invention to those skilled in the art. In the drawings, identical reference numerals denote the same or similar components having a same or similar function, unless specifically stated otherwise.

FIG. 1 is a schematic side view of a light-emitting diode (LED) tubular lighting device 1 according to an embodiment of the present invention. The LED tubular lighting device 1 may provide light, which may be referred to as device light. The LED tubular lighting device 1 comprises an elongated hollow tubular member 2, which has a first end 3 and a second end 4. The elongated hollow tubular member 2 comprising a light exit surface 5 extending in part between the first end 3 and the second end 4. The elongated hollow tubular member 2 may for example be made at least in part, or entirely, of quartz. Possibly, the light exit surface 5 may comprise at least one diffusing portion, or at least one diffuser, which for example may have a reflectance in a range between 12% and 25%.

In accordance with the embodiment of the present invention illustrated in FIG. 1, there is an opening (not shown in FIG. 1) in the elongated hollow tubular member 2 at each of the first end 3 and the second end 4. These openings may provide access to the interior of the elongated hollow tubular member 2. Further in accordance with the embodiment of the present invention illustrated in FIG. 1, the openings are closed by means of respective end closures 6 and 7, which in FIG. 1 are illustrated in the form of a caps. As illustrated in FIG. 1, each of the end closures 6 and 7 (e.g., caps) may include connections such as pins which may be used to mount the LED tubular lighting device 1 in a housing (not shown in FIG. 1) and/or provide connection of the LED tubular lighting device 1 to a power source (not shown in FIG. 1).

Figure 2:
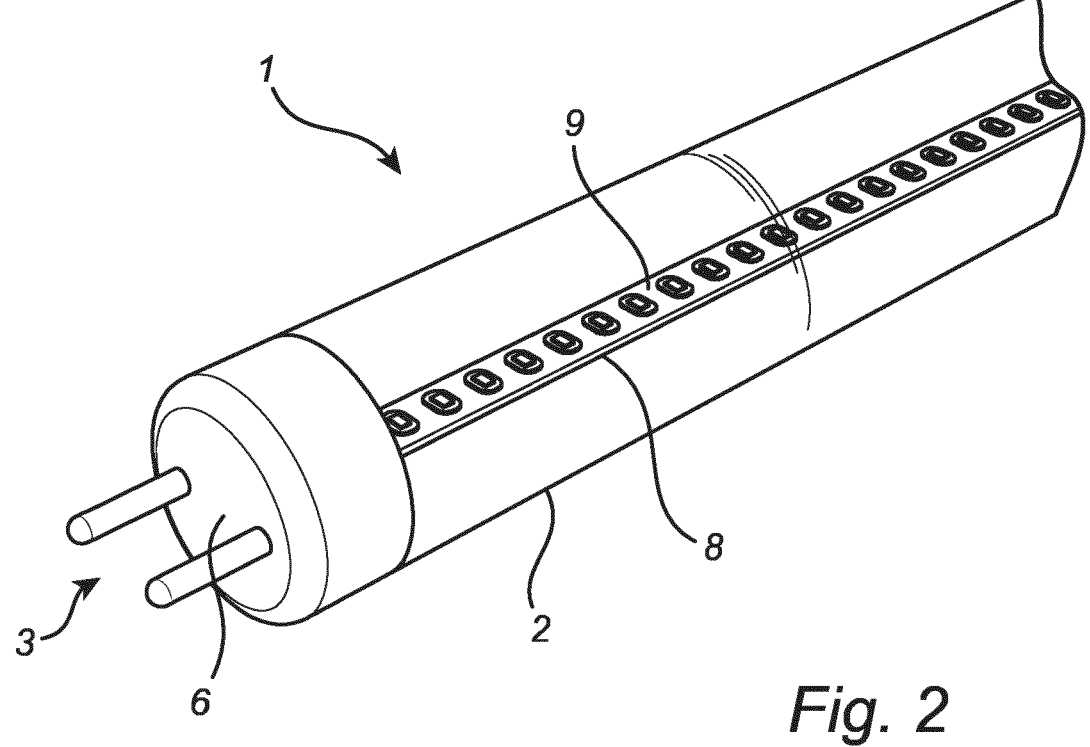
FIG. 2 is a schematic perspective view of a portion of a LED tubular lighting device according to an embodiment of the present invention.

FIG. 2 is a schematic perspective view of a portion of a LED tubular lighting device 1 according to an embodiment of the present invention. The LED tubular lighting device 1 illustrated in FIG. 2 is similar to the LED tubular lighting device illustrated in FIG. 1, and the same reference numerals in FIGS. 1 and 2 denote the same or similar components or elements having the same or similar function.

As illustrated in FIG. 2, the LED tubular lighting device 1 comprises an elongated carrier 8 (of which only a portion is shown in FIG. 2), which is arranged within the elongated hollow tubular member 2.

The LED tubular lighting device 1 comprises a plurality of LEDs, each of which is configured to, in operation, emit light. The plurality of LEDs comprises a plurality of first LEDs and a plurality of second LEDs. Each of the first LEDs is configured to emit violet light having a dominant peak wavelength in the range from 380 nm-420 nm. Each of the second LEDs is configured to emit ultraviolet light having a dominant peak wavelength in the range from 100 nm-380 nm. The plurality of LEDs may for example comprise at least twenty first LEDs. The plurality of LEDs may for example comprise at least eight second LEDs.

The elongated carrier 8 may for example be flexible. The elongated carrier 8 may for example comprise at least one printed circuit board (PCB), such as, for example, at least one flexible PCB.

In accordance with the embodiment of the present invention illustrated in FIG. 2, the elongated carrier 8 comprises a major surface 9, and the plurality of LEDs are arranged on the major surface 9.

As indicated in FIG. 2, the plurality of LEDs are arranged in a succession on the elongated carrier 8 such that at least some of the violet light emitted by the plurality of first LEDs and at least some of the ultraviolet light emitted by the plurality of second LEDs is emitted from the LED tubular lighting device 1 via the light exit surface (cf. FIG. 1) as the device light (i.e., the light provided by the LED tubular lighting device 1).

As will be described further in the following with reference to an exemplifying embodiment of the present invention illustrated in FIG. 3, the plurality of LEDs are arranged in the succession such that the distance between consecutive LEDs in the at least one succession varies over the succession while the distance between consecutive first LEDs in the at least one succession is constant, or substantially constant, over the succession. Although FIG. 2 indicates that there is a single succession of LEDs arranged on the elongated carrier 8, it is to be understood that there may be several successions of LEDs arranged on the elongated carrier 8, which for example may be running in parallel to each other.

Figure 3:
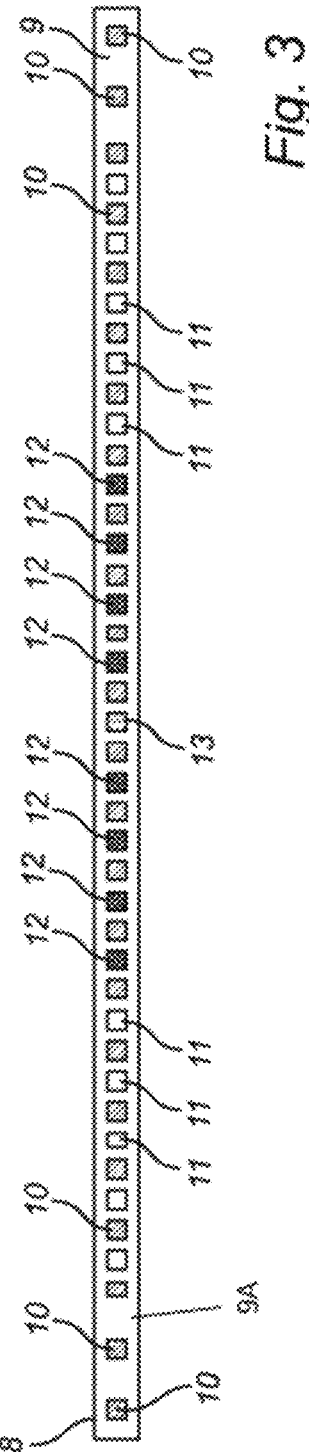
FIG. 3 is a schematic view of an elongated carrier of a LED tubular lighting device according to an embodiment of the present invention.

FIG. 3 is a schematic view of an elongated carrier 8 of a LED tubular lighting device according to an embodiment of the present invention.

The LED tubular lighting device comprises a plurality of LEDs, each of which is configured to, in operation, emit light. Just as in the embodiment of the present invention illustrated in FIG. 2, the elongated carrier 8 illustrated in FIG. 3 comprises a major surface 9, with the plurality of LEDs being arranged on the major surface 9.

The plurality of LEDs comprises a plurality of first LEDs 10 and a plurality of second LEDs 11, 12, 13. Each of the first LEDs 10 is configured to emit violet light having a dominant peak wavelength in the range 380 nm-420 nm. Each of the second LEDs 11, 12, 13 is configured to emit ultraviolet light having a dominant peak wavelength in the range 100 nm-380 nm.

It is to be noted that in addition to the major surface 9, the elongated carrier 8 might comprise another major surface (not shown in FIG. 3) that may be oppositely arranged from the major surface 8, and that some of the plurality of LEDs may be arranged on the major surface 9 and the other ones (e.g., the remaining ones) of the plurality of LEDs may be arranged on the other major surface.

A surface of the elongated carrier 8 on which the plurality of LEDs are arranged (e.g., the major surface 9 illustrated in FIG. 3) may be covered by a reflective material or reflective element 9A configured to reflect ultraviolet light impinging on the reflective material or reflective element. The reflective material or reflective element may have a reflectance of at least 85% in at least part of the ultraviolet C wavelength range.

The plurality of LEDs are arranged in a succession on the elongated carrier 8 such that at least some of the light emitted by the plurality of LEDs is emitted from the LED tubular lighting device via the light exit surface as the device light (i.e., the light provided by the LED tubular lighting device). The plurality of LEDs (including the first plurality of LEDs 10 and the second plurality of LEDs 11, 12, 13) are arranged in the succession such that the distance between consecutive LEDs in the succession varies over the succession while the distance between consecutive first LEDs 10 in the succession is constant, or substantially constant, over the succession. In other words, the pitch of the plurality of LEDs in the succession varies, while the pitch of the plurality of first LEDs 10 in the succession is constant, or substantially constant.

As illustrated in FIG. 3, the plurality of first LEDs 10 may be arranged over the entirety of the succession, whereas the plurality of second LEDs 11, 12, 13 may be arranged over only a part of the succession. For example, in accordance with the embodiment of the present invention illustrated in FIG. 2, the succession extends between the first end and the second end of the elongated hollow tubular member. The first end of the elongated hollow tubular member may be at the leftmost edge of the elongated carrier 8 illustrated in FIG. 3, and the second end of the elongated hollow tubular member may be at the rightmost edge of the elongated carrier 8 illustrated in FIG. 3. Further in accordance with the embodiment of the present invention illustrated in FIG. 3, the LED that is closest to the first end and the LED that is closest to the second end are not second LEDs. As illustrated in FIG. 3, the LED that is closest to the first end 3 and the LED that is closest to the second end 4 are both first LEDs 10.

In accordance with the embodiment of the present invention illustrated in FIG. 2, the second LEDs 11 are configured to emit ultraviolet light having a dominant peak wavelength in the ultraviolet A wavelength range, the second LEDs 12 are configured to emit ultraviolet light having a dominant peak wavelength in the ultraviolet B wavelength range, and the second LED 13 is configured to emit ultraviolet light having a dominant peak wavelength in the ultraviolet C wavelength range.

As illustrated in FIG. 3, the second LED 13 configured to emit ultraviolet light having a dominant peak wavelength in the ultraviolet C wavelength range may be arranged in the succession between at least one of the second LEDs 11 configured to emit ultraviolet light having a dominant peak wavelength in the ultraviolet A wavelength range and at least one of the second LEDs 12 configured to emit ultraviolet light having a dominant peak wavelength in the ultraviolet B wavelength range.

It is noted that only some of the first LEDs 10 are indicated by reference numerals in FIG. 3, and also that only some of the second LEDs 11 are indicated by reference numerals in FIG. 3. It is to be understood that the number of first LEDs 10 and the number of second LEDs 11, 12, 13 illustrated in FIG. 3 are according to examples, and that the number of first LEDs 10 and/or the number of second LEDs 11, 12, 13 may be different from what is illustrated in FIG. 3. Further, the number of second LEDs 11, the number of second LEDs 12, and the number of second LEDs 13 are also according to examples, and it is to be understood that that the number of second LEDs 11, the number of second LEDs 12, and the number of second LEDs 13 may be different from what is illustrated in FIG. 3. For example, there may be more than one second LED 13 (i.e., LED configured to emit ultraviolet light having a dominant peak wavelength in the ultraviolet C wavelength range) included in the LED tubular lighting device. The plurality of LEDs included in the LED tubular lighting device may for example comprise at least twenty first LEDs and at least eight second LEDs.

With further reference to FIG. 1, the LED tubular lighting device 1 may comprise a controller, schematically indicated at 15 in FIG. 1. The location of the controller 15 in the LED tubular lighting device 1 is exemplifying and not limiting. For example, while FIG. 1 indicates that the controller 15 is arranged within the elongated hollow tubular member 2, it could instead be arranged outside the elongated hollow tubular member 2.

With further reference to FIGS. 1 and 3, the controller, or control device, control unit or control module, 15 may be configured to control operation of each of the plurality of LEDs at least with respect to switching on and switching off the LED. The controller 15 may be configured to individually control each of the first plurality of LEDs 10. The controller 15 may be configured to individually control each of the second plurality of LEDs 11, 12, 13. The controller 15 may be configured to control operation of each of at least some of the plurality of LEDs with respect to intensity and/or wavelength of the light emitted by the LED. For example, the controller 15 may be configured to control operation of each of some or all of the plurality of second LEDs 11, 12, 13 with respect to intensity and/or wavelength of the light emitted by the second LED 11, 12, 13. Possibly, for each or any of the second LEDs 11, 12, 13, the controller 15 may be configured to control the intensity and/or wavelength of the ultraviolet light emitted by the second LED 11, 12, 13, e.g., based on desired intensity and/or wavelength of the ultraviolet light emitted by the LED tubular lighting device 1 and based on measurements of these quantities by a sensor (not shown in the figures). According to one or more example implementations, the controller 15 may be configured to individually control the intensity of violet light emitted by the plurality of first LEDs 10 and the intensity of ultraviolet light emitted by the plurality of second LEDs 11, 12, 13, wherein the ratio between the intensity of violet light emitted by the plurality of first LEDs 10 and the intensity of ultraviolet light emitted by the plurality of second LEDs 11, 12, 13 may be varied by the controller 15.

In conclusion, a LED tubular lighting device is disclosed, comprising an elongated hollow tubular member and a plurality of LEDs. The plurality of LEDs comprise at least a plurality of first LEDs, wherein each of the first LEDs is configured to emit violet light, and a plurality of second LEDs, wherein each of the second LEDs is configured to emit ultraviolet light. The LED tubular lighting device comprises an elongated carrier arranged within the elongated hollow tubular member. The plurality of LEDs are arranged in at least one succession on the elongated carrier, wherein the plurality of LEDs are arranged in the at least one succession such that the distance between consecutive LEDs in the at least one succession varies over the at least one succession while the distance between consecutive first LEDs in the at least one succession is constant over the at least one succession.

While the present invention has been illustrated in the appended drawings and the foregoing description, such illustration is to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light emitting diode, LED, tubular lighting device arranged to provide device light, the LED tubular lighting device comprising:

an elongated hollow tubular member having a first end and a second end, the elongated hollow tubular member comprising a light exit surface (5) extending at least in part between the first end and the second end;

a plurality of LEDs, each of which is configured to, in operation, emit light, the plurality of LEDs comprising at least a plurality of first LEDs, wherein each of the first LEDs is configured to emit violet light having a dominant peak wavelength in the range 380 nm-420 nm, and a plurality of second LEDs, wherein each of the second LEDs is configured to emit ultraviolet light having a dominant peak wavelength in the range 100 nm-380 nm; and an elongated carrier arranged within the elongated hollow tubular member, wherein the plurality of LEDs are arranged in at least one succession on the elongated carrier such that at least some of the violet light emitted by the plurality of first LEDs and at least some of the ultraviolet light emitted by the plurality of second LEDs is emitted from the LED tubular lighting device via the light exit surface as the device light, wherein the plurality of LEDs are arranged in the at least one succession such that a distance between at least some consecutive LEDs in the at least one succession varies over the at least one succession while a distance between consecutive first LEDs in the at least one succession is constant over the at least one succession.

2. A LED tubular lighting device according to claim 1, wherein the at least one succession extends between the first end and the second end, and wherein the LED that is closest to the first end and the LED that is closest to the second end are not second LEDs.

3. A LED tubular lighting device according to claim 1, wherein each or any of the second LEDs is configured to emit ultraviolet light having a dominant peak wavelength in an ultraviolet C wavelength range, or wherein each or any of the second LEDs is configured to emit ultraviolet light having a dominant peak wavelength in an ultraviolet A wavelength range or in an ultraviolet B wavelength range.

4. A LED tubular lighting device according to claim 1, wherein at least one of the second LEDs is configured to emit ultraviolet light having a dominant peak wavelength in an ultraviolet A wavelength range, at least one of the second LEDs is configured to emit ultraviolet light having a dominant peak wavelength in an ultraviolet B wavelength range, and at least one of the second LEDs is configured to emit ultraviolet light having a dominant peak wavelength in an ultraviolet C wavelength range.

5. A LED tubular lighting device according to claim 4, wherein at least one of the second LEDs configured to emit ultraviolet light having a dominant peak wavelength in the ultraviolet C wavelength range is arranged in the at least one succession between at least one of the second LEDs configured to emit ultraviolet light having a dominant peak wavelength in the ultraviolet A wavelength range and at least one of the second LEDs configured to emit ultraviolet light having a dominant peak wavelength in the ultraviolet B wavelength range.

6. A LED tubular lighting device according to claim 1, wherein the light exit surface comprises a diffuser.

7. A LED tubular lighting device according to claim 6, wherein the diffuser has a reflectance in a range between 12% and 25%.

8. A LED tubular lighting device according to claim 1, wherein the plurality of first LEDs and the plurality of second LEDs are arranged in the at least one succession such that a distance between consecutive second LEDs in the at least one succession is larger than the distance between consecutive first LEDs in the succession over at least a part of the at least one succession.

9. A LED tubular lighting device according to claim 1, wherein the plurality of first LEDs are arranged over an entirety of the at least one succession whereas the plurality of second LEDs are arranged over only a part of the at least one succession.

10. A LED tubular lighting device according to claim 1, wherein each of the first LEDs is configured to emit violet light having a same intensity, and wherein at least some of the second LEDs are configured to emit ultraviolet light having different intensity.

11. A LED tubular lighting device according to claim 1, further comprising a controller configured to individually control an intensity of violet light emitted by the plurality of first LEDs and an intensity of ultraviolet light emitted by the plurality of second LEDs, wherein the controller is arranged to vary a ratio between the intensity of violet light emitted by the plurality of first LEDs and the intensity of ultraviolet light emitted by the plurality of second LEDs.

12. A LED tubular lighting device according to claim 1, wherein a surface of the elongated carrier on which the plurality of LEDs are arranged is covered by a reflective material or reflective element configured to reflect ultraviolet light impinging on the reflective material or reflective element and having a reflectance of at least 85% in at least part of an ultraviolet C wavelength range, the ultraviolet C wavelength range extending between 100 nm to 280 nm.

13. A LED tubular lighting device according to claim 1, wherein the first end and the second end comprise pins configured to mechanically and electrically connect the LED tubular lighting device to a luminaire or lamp.

14. A luminaire or lamp comprising at least one LED tubular lighting device according to claim 1.

\* \* \* \* \*